United States Patent [19]
Wijkamp et al.

[11] Patent Number: 5,215,614
[45] Date of Patent: Jun. 1, 1993

[54] METHOD FOR MANUFACTURING A CATHETER

[75] Inventors: A. C. J. M. Wijkamp, Roden; R. Antoni, Gronigen; G. Jansman, Roden; H. W. Wegereef, Peize, all of Netherlands

[73] Assignee: Cordis Europa N.V., Roden, Netherlands

[21] Appl. No.: 546,019

[22] Filed: Jun. 28, 1990

[30] Foreign Application Priority Data

Jun. 29, 1989 [NL] Netherlands ............... 89.01654

[51] Int. Cl.⁵ .................................. B29C 65/06
[52] U.S. Cl. ...................... 156/153; 156/244.18; 156/304.6; 264/139; 264/162
[58] Field of Search ............ 264/139, 162, 513, 514; 156/304.2, 304.6, 153, 244.18

[56] References Cited

U.S. PATENT DOCUMENTS

| | | | |
|---|---|---|---|
| 3,860,468 | 1/1975 | Scherer | 156/304.2 |
| 3,890,976 | 6/1975 | Bazell et al. | 604/96 |
| 4,385,635 | 5/1983 | Ruiz | 128/658 |
| 4,495,134 | 1/1985 | Ouchi et al. | 264/516 |
| 4,551,292 | 11/1985 | Fletcher et al. | 264/139 |
| 4,596,563 | 6/1986 | Pande | 604/264 |
| 4,636,346 | 1/1987 | Gold et al. | 264/162 |
| 4,753,765 | 6/1988 | Pande | 264/149 |

FOREIGN PATENT DOCUMENTS 2188448  1/1974  France.
2016274  9/1979  United Kingdom.

Primary Examiner—Jay H. Woo
Assistant Examiner—Robert B. Davis
Attorney, Agent, or Firm—Lockwood, Alex, Fitzgibbon & Cummings

[57] ABSTRACT

A method of making a catheter is provided. The catheter has an atraumatic portion at the distal end of a catheter having the stiffness and torque resistance required of a catheter such as that suitable for angiographic uses, typically in French sizes on the order of about 2 to about 8. The atraumatic tip portion has a generally co-axially layered structure. An inner layer is made of soft atraumatic polymer, and an outer layer is made of a polymer to impart needed stiffness and torque properties to the catheter. In the preferred embodiment, a portion of the distal tip material of the harder outer layer is removed, thereby exposing the inner, atraumatic material for initial engagement with internal body passageways.

4 Claims, 3 Drawing Sheets

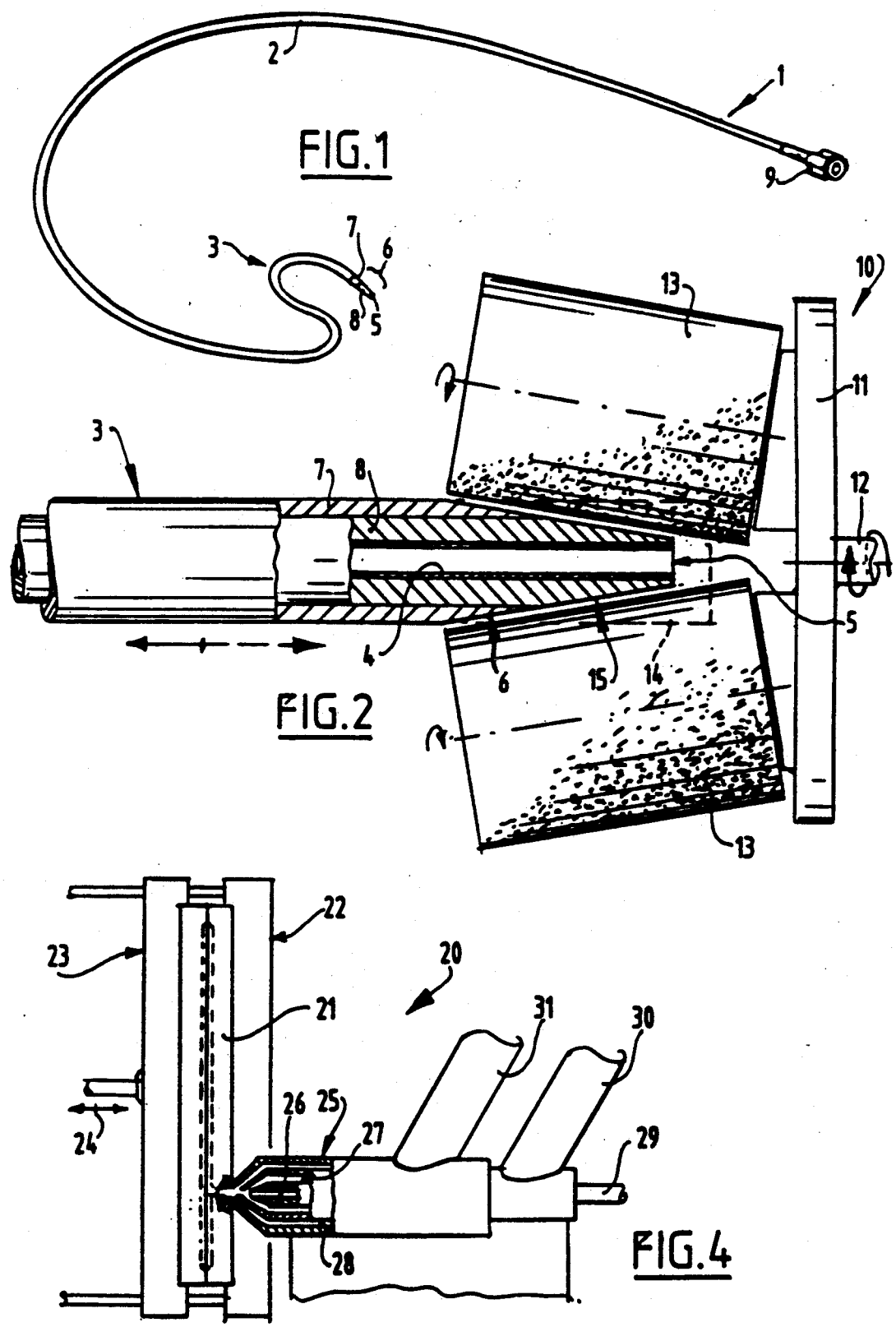

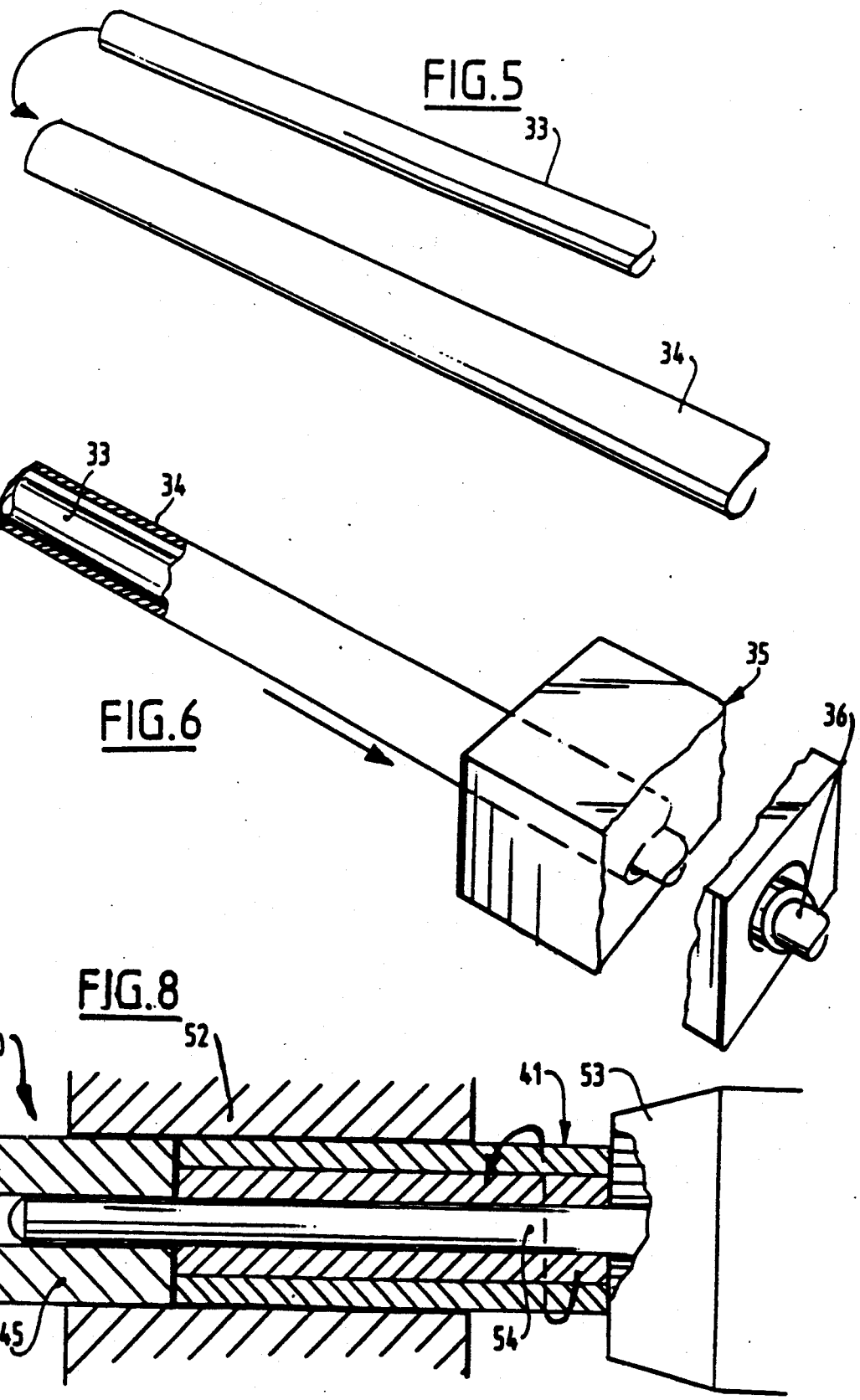

METHOD FOR MANUFACTURING A CATHETER

DESCRIPTION

Background and Summary of the Invention

The invention relates to a method for the manufacture of a catheter, more particularly to the manufacture of a catheter having an elongated, flexible, tubular body with at least one central channel, a coupling element at the proximal end portion of the catheter, and a distal or tip end portion which is made by forming a taper on a part of the distal end such that this part acquires a decreasing diameter toward the outermost distal tip.

As is generally known in the manufacture of catheters, their tubular bodies are manufactured from material which gives the finished catheter certain required properties, such as flexibility and torsional stiffness. The outlet or distal end of a catheter can be pointed in order to facilitate the introduction of the catheter into a patient. This forming of the point is of course not performed such that a sharp point or sharp end results, inasmuch as this could entail the risk of internal injury during insertion. Even with prior art catheters that do have a pointed distal end, there does nevertheless exist a possible risk of internal injury with the insertion of catheters manufactured by previously known methods, in particular damage to a vascular wall for instance.

A general object of the present invention is to provide a method for the manufacture of a catheter having characteristics such that any risk of internal injury is minimized.

With the method according to the invention, an especially atraumatic catheter is provided by having the body formed, or at least the tip end portion thereof, with a number of co-axial layers, an inner layer of which is made of a material softer than a layer situated to the outside thereof and whereby, during forming of a pointed tip portion, material is removed from the outer periphery. As a result, the softer layer situated more to the interior is exposed during forming of the pointed tip portion so that the outermost surface of the pointed tip portion of the catheter is formed by this soft material. The required stiffness of at least the end portion is obtained by choosing a stiffer material for the layer or layers situated to the outside of the softer interior layer. As a result, the total stiffness of the assembled end is accomplished according to the needs of the catheter.

Because the outermost part of the pointed tip portion of the catheter is formed of the soft material, and because this is the material which is exposed according to the invention, the risk of internal injury during insertion of the catheter into a patient is greatly reduced.

It has been found that the required effect of the invention is achieved to a suitable degree if the outlet end of the catheter has two co-axial layers. In view of its simplicity, this structure is preferred. In addition to the two structural layers, the catheter can also have a thin innermost layer of friction-reducing material in order to facilitate passage through the catheter.

The catheter can consist of two or more co-axial layers throughout its length. However, it is typically preferred that the tip portion and the body portion are separately formed and joined together. The body portion or basic part can then be manufactured in a manner such that it has optimal qualities in respect of compression strength and torsional stiffness, which requirements are of secondary importance for the end or tip portion.

A favorable embodiment of the method according to the invention is one in which the end or tip portion is formed by injection molding with the simultaneous supply of multiple materials. This type of coextrusion is well known in the art.

When mass production volumes are desired, it is preferred that the end or tip portion be formed by forming a coextrusion of a continuous length and then dividing the continuous length. The basic material which consists of at least two co-axial layers can in this way be manufactured in greater lengths in a suitable manner, whereafter the required end portions thereof can be separated, for example by being cut or sliced off.

The invention also relates to and provides a catheter comprising an elongated, flexible tubular body having at least one central channel whereby the body is provided at one end with a proximal end coupling element and has at the other end at least one outlet opening, whereby this outlet or distal end is given a point, as a result of which it has a decreasing diameter over a portion towards the outermost distal end or tip.

According to this invention, this catheter has the feature that at least at the outlet end it consists of a number of co-axial layers, an inner layer of which is of softer material than a layer situated more to the outside, and whereby as a result of a pointed end portion being formed, the layer situated more to the outside is removed at the position of the outermost pointed end portion.

The invention will be further elucidated in the following description with reference to the accompanying drawings.

BRIEF DESCRIPTION OF THE DRAWINGS

FIG. 1 shows in schematic perspective view a catheter manufactured with the method according to the invention.

FIG. 2 shows schematically a grinding device for carrying out a step in the method according to the invention.

FIG. 4 shows schematically a portion of an injection molding device suitable for use with the method according to the invention.

FIGS. 5 and 6 illustrate an alternative approach for carrying out the method according to the invention.

FIGS. 7 and 8 each schematically show a step which can be incorporated into embodiments of the method according to the invention.

DETAILED DESCRIPTION OF THE INVENTION

Figure 3:
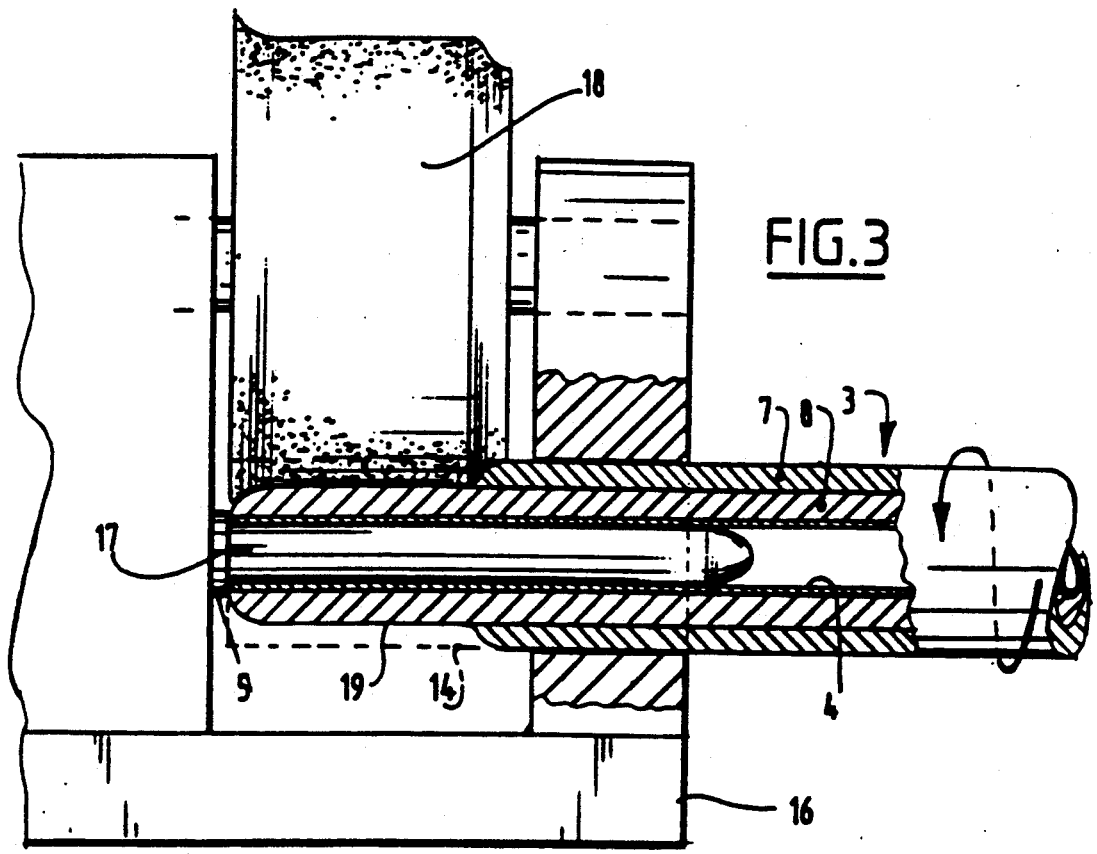
FIG. 3 shows an alternative grinding device which can be used in place of the device shown in FIG. 2.

The catheter 1 shown in FIG. 1 is a catheter which is intended for angiographic tests. The catheter 1 has an elongated, flexible, tubular body 2 having a central channel, and it is made in a generally known manner. Arranged at one end, namely the proximal end portion, of the body 2 is a coupling element 9 of generally known construction. Situated close to the other or distal end is an end portion 3 which in the embodiment of the catheter shown is arranged plastically in a particular form, depending on the intended application. At the outer end the central channel has an outlet opening 5. The end portion 3 is brought to a point so that this portion 3 has a decreasing outer diameter over a determined distance 6 towards the outermost point. The diameter can decrease uniformly as shown in FIG. 2, but in another embodiment, this decrease can be in a stepped manner.

In accordance with an important aspect of the invention, at least the distal end portion close to the outermost point, that is the outlet end, is formed with a number of structural co-axial layers. In the illustrated embodiment, the distal end or tip portion has two structural co-axial layers, 7 and 8. The inner layer 8 is made of a material which is softer than the layer 7 situated more to the outside, and during forming of the pointed end portion, material is removed from the outer periphery. In the embodiment shown in FIG. 2, a thin layer 4 of friction reducing material is situated within the central channel of the inner layer 8.

One embodiment of the method is illustrated in FIG. 2, and the structure of the end portion 3 having layers 7, 8 and 4 is clearly seen in this view. For forming the pointed end portion, use is made of a diagrammatically illustrated grinding device 10 which includes a bearing plate 11 that is fixedly connected to a rotatable shaft 12. Bearing plate 11 supports a number of grinding stones 13, preferably three of them, which are rotatably connected to the bearing plate 11, whereby the axis of rotation of each grinding stone 13 lies at a taper angle. Instead of this illustrated arrangement, the grinding stones 13 can also be conical and mounted with their respective axes of rotation perpendicular to the bearing plate 11. The grinding stones 13 are planetarily driven. A grinding device such as the grinding device 10 is in itself known and is for example already employed for forming a pointed end of prior art catheters. Structural and mechanical specifics of this type of device are appreciated by the art and will not be further described in detail.

The arrangement illustrated in FIG. 2 effects a uniform diameter reduction towards the distal end of the catheter, whereby during forming of the pointed end portion, a cone-shaped sloping surface 15 is formed. FIG. 3 illustrates an arrangement in which the diameter reduction is performed in stepped manner. The end of the catheter 3 is fixed in a mold 16. The mold 16 is provided with a mandrel 17 which can protrude into the central channel of the catheter 3. The grinding stone 18 has a profile formed such that, at the position of the outermost point, the harder layer 7 can be ground away and rounded transitions are formed. During grinding, the catheter 3 is rotated so that the entire periphery is uniformly machined. The final result is a stepped surface 19 at the distal end portion of the catheter.

It will be apparent from FIGS. 2 and 3 that as a result of a pointed end portion being formed with a grinding device, whereby material is removed from the original outer periphery 14 in order to form the sloping surface 15 or the stepped surface 19, the harder outer layer 7 is entirely removed at the outermost portions of the pointed end portion. As a result, the inner layer 8 protrudes freely at the outer distal end tip of the catheter.

According to the invention, a relatively soft material is chosen as the material of the inner layer 8 so that the outermost distal end pointed tip of the catheter 1 is made of this softer material, the harder material having been removed thereat. This soft profile assures that there is a minimal risk of internal injury during insertion of the catheter into the patient.

In order to nevertheless obtain the required stiffness of the end portion 3, material with a greater stiffness is chosen for the outer layer 7 of this end portion 3. The stiffness of the combined layers 7 and 8 can as a result be brought to a required value. Identities of the types of softer and harder materials which are suitable for internal use as a catheter material are known generally in the art and include polymers of various types, including polyolefins, polyesters, polyamides, polyurethanes and the like.

For certain applications, the catheter 1 can consist over its entire length of at least two co-axial layers. Preferably, however, the end portion 3 is separately formed and later joined to a basic part or body portion of the catheter. The formation of an end or tip portion of the catheter. The formation of an end or tip portion having a number of layers can take place according to a preferred aspect of the invention with the simultaneous supply and coextrusion of a number of different materials. In FIG. 4, an injection molding device is shown schematically whereby three materials can be supplied simultaneously for the formation of an end portion with three co-axial layers.

As is known, such an injection device 20 comprises a mold holder 22, 23 wherein the two parts of a mold 21 are arranged such that they can be moved in the direction of the arrow 24 away from and toward one another. In FIG. 4 the parts of the mold 21 are shown in the closed position, or moved toward one another. In this situation, a mold cavity is defined between the mold parts which can be filled with plastic in liquid form. This takes place using a die 25. With an injection molding device for the simultaneous injection of a number of materials, the die 25 takes a multiple form as shown. This comprises three injection channels 26, 27 and 28 which are connected to supply connections 29, 30 and 31 respectively. Through a suitable choice of supply pressure and speed of the respective materials through the die 25, a layered object will be formed in the mold cavity of the mold 21. With the present method, the mold cavity will of course have the form of an elongate channel with an annular section.

Another method for manufacturing at least an end portion is shown schematically in FIGS. 5 and 6. Separately manufactured are a tube or hose 33 of the soft material for the inner layer and an outer tube or hose 34 of harder material for an outer layer. The tube 34 is manufactured with an internal diameter which is somewhat smaller than the outer diameter of the tube 33.

The tube 34 is subsequently heated and expanded in its heated state. In the expanded state the tube 34 is cooled so that the hose is "frozen" in the expanded state. The tube 33 is then pushed into the tube 34. The assembly of both tubes is guided through heating mold 35, resulting in the outer layer tube 34 being heated to a temperature such that it again "thaws" to its original shape and diameter size. The catheter material 36 leaving the heating mold 35 thus comprises two co-axial layers of material whereby the inner layer is made of a material that is softer than the material of the outer layer. The outer layer grips firmly around the inner layer so that they together form one whole catheter or end portion.

When an embodiment of the method according to the invention is applied whereby the end portion consisting of at least two layers is separately manufactured, this separately manufactured end portion must be fixed in place onto a basic part or body portion. For purposes of illustration and description, two possible joining methods are mentioned and shown schematically in FIGS. 7 and 8.

Figure 7:
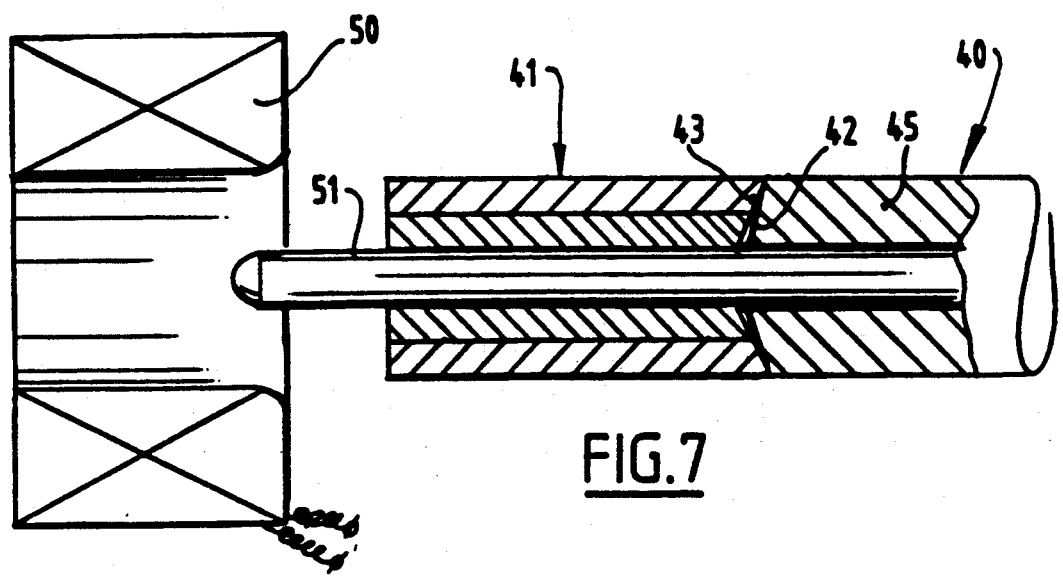

In the FIG. 7 arrangement, the catheter 40 consists of a basic part or elongated body 45 and an end or tip portion 41. The basic part 45 and the end portion 41 are pushed onto a mandrel 51 such that the respective end faces 42 and 43 lie against one another. The catheter parts thus pushed up against one another onto the mandrel 51 are inserted into a heating mold 50. The assembly is inserted so far into the mold 50 that the end faces 42, 43 are located substantially in the middle thereof. By switching on the heating mold 50, the material of both the basic part 45 and the end portion 41 are heated such that they melt and flow together. In this way, the end portion 41 is welded onto the basic part 45, and after cooling they form one whole unitarily assembled catheter.

A second option is shown in FIG. 8. The end portion 41 is pushed onto a mandrel 54 which is attached to a rotatable bearer 53. The mandrel protrudes beyond the end portion 41, and the basic part 45 slides onto this protruding end. By now setting the bearer 53, and therewith the end portion 41, into rotation and pressing the basic part 45 to the right as seen in FIG. 8 while the basic part is held against rotation, so much heat will arise through fiction at the location of the contact surfaces that parts 41 and 45 will melt together. For the guiding and enclosing of the melting material a stationary mold 52 is used. The press-on force for the basic part 45 and the time during which the bearer 53 must be rotated typically are determined empirically. The weld obtained between the end portion and the basic part is further finished in order to achieve a uniform transition from the basic part 45 to the end portion 41.

Forming of the pointed end portion according to this invention normally takes place after the end portion 41 has been affixed to the basic part 45, whether this is accomplished by a procedure as illustrated in FIG. 7 or FIG. 8, or by any other joining procedure suitable for catheter components and materials.

It will be understood that the embodiments of the present invention which have been described are illustrative of some of the applications of the principles of the present invention. Numerous modifications may be made by those skilled in the art without departing from the true spirit and scope of the invention.

We claim:

1. In a method for manufacturing a catheter, including the steps of:
    manufacturing an elongated, flexible, tubular body having at least one central channel therethrough, and a coupling element at a proximal end portion of the elongated tubular body;
    forming a distal end portion having a channel and an outlet opening therethrough, the distal end portion being pointed and at a distal end of the elongated tubular body such that this portion acquires a decreasing diameter towards the outermost distal end tip of the catheter, wherein the improvement comprises:
    said forming step includes providing a co-axial portion having a plurality of co-axial layers, wherein an inner layer of the co-axial layers is made of a relatively soft material that has atraumatic characteristics, the relatively soft material being more atraumatic than said body and having a hardness substantially less than the hardness of an outermost layer of the co-axial layers of the co-axial end portion;
    said forming step further includes removing the entirety of a substantial defined length of the outermost layer of the distal tip end of the co-axial end portion and thereby exposing a distal tip portion length of the atraumatic inner layer in order to form a pointed end portion from said relatively soft inner layer material which is and which totally defines said atraumatic distal end tip of the catheter that is integral with said inner layer of the coaxial layers thereby providing a finally formed atraumatic distal end catheter tip, said atraumatic distal end catheter tip having a length substantially the same as said substantial defined length of the outermost layer removed during said removing step;
    separately forming the elongated tubular body and said distal end portion whereby said distal end portion includes both said atraumatic distal end catheter tip and a length of said coaxial portion remaining after said removing step, said elongated tubular body having a radially extending, distal axial end contact surface substantially perpendicular to the axis of the tubular body, and said length of coaxial portion having a radially extending proximal axial end contact surface substantially perpendicular to the axis of the distal end portion; and
    joining said elongated tubular body and said distal end portion by rotating said distal end portion with respect to said elongated tubular body while their respective opposing radially extending axial end contact surfaces engage one another, whereby friction melts the contact surfaces to bond them together.

2. The method as claimed in claim 1, wherein said forming step provides two co-axial layers, one being said relatively soft, atraumatic inner layer and the other being said harder outermost layer.

3. The method as claimed in claim 1, wherein said co-axial end portion is formed by coextrusion through injection molding with simultaneous supply of a plurality of different materials, one of said materials being for the inner layer and another of said materials being for the outermost layer.

4. The method as claimed in claim 3, wherein the co-axial end portion forming step includes dividing an elongated coextrusion into a plurality of the co-axial end portions.

* * * * *